United States Patent
Cohen et al.

(10) Patent No.: US 9,679,499 B2
(45) Date of Patent: Jun. 13, 2017

(54) SYSTEMS AND METHODS FOR SENSING HAND MOTION BY MEASURING REMOTE DISPLACEMENT

(75) Inventors: Robert F. Cohen, Kensington, MD (US); Mark S. Meents, Germantown, MD (US)

(73) Assignee: Immersion Medical, Inc., Baltimore, MD (US)

( * ) Notice: Subject to any disclaimer, the term of this patent is extended or adjusted under 35 U.S.C. 154(b) by 1953 days.

(21) Appl. No.: 12/210,825

(22) Filed: Sep. 15, 2008

(65) Prior Publication Data
US 2010/0069941 A1 Mar. 18, 2010

(51) Int. Cl.
*G09B 23/28* (2006.01)
*A61B 19/00* (2006.01)
(Continued)

(52) U.S. Cl.
CPC .......... *G09B 23/285* (2013.01); *A61B 34/70* (2016.02); *A61B 34/74* (2016.02); *A61B 90/06* (2016.02);
(Continued)

(58) Field of Classification Search
CPC .... A61B 2019/4857; A61B 2017/2829; A61B 2017/2906; A61B 2017/2919; A61B 2017/2922; A61B 2017/2926; A61B 2017/2931; A61B 2017/2932; A61B 2017/2939; A61B 2017/294; A61B 2017/2941; A61B 2017/2947;
(Continued)

(56) References Cited

U.S. PATENT DOCUMENTS 3,785,381 A 1/1974 Lower et al.
4,038,987 A * 8/1977 Komiya ............... A61B 17/122
606/142
(Continued)

FOREIGN PATENT DOCUMENTS

DE 10258952 8/2004
DE 103 13 912 10/2004
(Continued)

OTHER PUBLICATIONS

Basdogan, C. et al., Virtual Environments for Medical Training: Graphical and Haptic Simulation of Laparoscopic Common Bile Duct Exploration, IEEE/ASME Transactions on Mechatronics, vol. 6, No. 3, 2001.
(Continued)

*Primary Examiner* — Melanie Tyson
*Assistant Examiner* — Erin Colello
(74) *Attorney, Agent, or Firm* — Kilpatrick Townsend & Stockton LLP

(57) ABSTRACT

Systems and methods for sensing hand motion by measuring remote displacement are disclosed. For example, one disclosed apparatus includes a first surface configured to engage a first distal member of a surgical tool and a second surface configured to engage a second distal member of the surgical tool, the second surface coupled to the first surface at a pivot point. The apparatus further includes a sensor configured to detect a relative movement of the first surface and the second surface about the pivot point and to generate a signal based at least in part on the relative movement.

21 Claims, 10 Drawing Sheets

(51) Int. Cl.
*A61B 34/00* (2016.01)
*A61B 17/00* (2006.01)
*A61B 90/00* (2016.01)

(52) U.S. Cl.
CPC ............ *A61B 2017/00725* (2013.01); *A61B 2090/067* (2016.02)

(58) Field of Classification Search
CPC . A61B 17/30; A61B 2562/00; A61B 2562/02; A61B 2562/0247; A61B 2562/0261; A61B 2562/0257; A61B 2562/0266; A61B 2562/16; A61B 2560/0462; A61B 19/50; A61B 2019/501; A61B 2019/502; A61B 2019/504; A61B 2019/507; A61B 2019/508; A61B 2018/00297–2018/00309; A61B 2017/00725; A61B 34/70; A61B 34/72; A61B 34/74; A61B 2034/741; A61B 2034/742; A61B 2034/743; A61B 2034/744; A61B 34/75; A61B 34/76; A61B 34/77; A61B 34/30; A61B 2034/305; A61B 34/35; A61B 34/37; G09B 23/28–23/288; G09B 23/285
USPC ................................ 606/208, 170, 130, 211
See application file for complete search history.

(56) References Cited

U.S. PATENT DOCUMENTS

| | | | |
|---|---|---|---|
| 4,847,987 A | 7/1989 | Ballard | |
| 4,961,138 A | 10/1990 | Gorniak | |
| 5,015,249 A * | 5/1991 | Nakao | A61B 17/10 227/901 |
| 5,047,046 A | 9/1991 | Bodoia | |
| 5,049,153 A * | 9/1991 | Nakao | A61B 17/10 606/138 |
| 5,088,046 A | 2/1992 | McMurtry | |
| 5,148,377 A | 9/1992 | McDonald | |
| 5,181,181 A | 1/1993 | Glynn | |
| 5,188,111 A | 2/1993 | Yates et al. | |
| 5,209,747 A * | 5/1993 | Knoepfler | 606/16 |
| 5,222,961 A * | 6/1993 | Nakao | A61B 17/10 606/142 |
| 5,273,038 A | 12/1993 | Beavin | |
| 5,296,846 A | 3/1994 | Ledley | |
| 5,339,799 A * | 8/1994 | Kami | A61B 18/14 600/109 |
| 5,383,880 A * | 1/1995 | Hooven | 606/142 |
| 5,389,849 A | 2/1995 | Asano et al. | |
| 5,411,511 A | 5/1995 | Hall | |
| 5,482,472 A | 1/1996 | Garoni et al. | |
| 5,503,320 A | 4/1996 | Webster et al. | |
| 5,546,943 A | 8/1996 | Gould | |
| 5,609,485 A | 3/1997 | Bergman et al. | |
| 5,609,607 A | 3/1997 | Hechtenberg et al. | |
| 5,623,582 A * | 4/1997 | Rosenberg | 700/264 |
| 5,649,934 A | 7/1997 | Smeltzer, III et al. | |
| 5,685,474 A | 11/1997 | Seeber | |
| 5,724,264 A | 3/1998 | Rosenberg et al. | |
| 5,728,044 A | 3/1998 | Shan | |
| 5,769,640 A | 6/1998 | Jacobus et al. | |
| 5,771,902 A | 6/1998 | Lee et al. | |
| 5,792,135 A * | 8/1998 | Madhani et al. | 606/1 |
| 5,810,880 A | 9/1998 | Jensen et al. | |
| 5,828,197 A * | 10/1998 | Martin et al. | 318/567 |
| 5,833,634 A | 11/1998 | Laird et al. | |
| 5,836,894 A | 11/1998 | Sarvazyan | |
| 5,882,206 A | 3/1999 | Gillio | |
| 5,913,876 A * | 6/1999 | Taylor et al. | 607/2 |
| 5,928,158 A | 7/1999 | Aristides | |
| 5,950,629 A | 9/1999 | Taylor et al. | |
| 5,956,040 A | 9/1999 | Asano et al. | |
| 5,965,880 A | 10/1999 | Wolf et al. | |
| 5,971,767 A | 10/1999 | Kaufman et al. | |
| 5,976,159 A * | 11/1999 | Bolduc et al. | 606/142 |
| 5,989,199 A | 11/1999 | Cundari et al. | |
| 6,063,031 A | 5/2000 | Cundari et al. | |
| 6,086,606 A * | 7/2000 | Knodel et al. | 606/208 |
| 6,096,004 A | 8/2000 | Meglan et al. | |
| 6,132,441 A | 10/2000 | Grace | |
| 6,142,994 A * | 11/2000 | Swanson | A61B 18/1482 606/41 |
| 6,152,920 A * | 11/2000 | Thompson | A61B 18/1492 600/374 |
| 6,190,334 B1 | 2/2001 | Lasky et al. | |
| 6,193,519 B1 | 2/2001 | Eggert et al. | |
| 6,210,168 B1 | 4/2001 | Aiget et al. | |
| 6,219,589 B1 * | 4/2001 | Faraz et al. | 700/254 |
| 6,223,100 B1 * | 4/2001 | Green | 700/264 |
| 6,273,902 B1 * | 8/2001 | Fogarty | A61B 17/282 606/207 |
| 6,287,322 B1 * | 9/2001 | Zhu | A61B 17/0057 606/108 |
| 6,308,104 B1 * | 10/2001 | Taylor et al. | 607/118 |
| 6,309,397 B1 * | 10/2001 | Julian et al. | 606/130 |
| 6,325,808 B1 * | 12/2001 | Bernard et al. | 606/139 |
| 6,375,471 B1 | 4/2002 | Wendlandt et al. | |
| 6,377,011 B1 * | 4/2002 | Ben-Ur | 318/566 |
| 6,381,499 B1 * | 4/2002 | Taylor et al. | 607/118 |
| 6,428,070 B1 * | 8/2002 | Takanashi et al. | 294/207 |
| 6,436,107 B1 | 8/2002 | Wang et al. | |
| 6,494,882 B1 | 12/2002 | Lebouitz et al. | |
| 6,551,316 B1 * | 4/2003 | Rinner et al. | 606/57 |
| 6,594,552 B1 | 7/2003 | Nowlin et al. | |
| 6,623,433 B2 | 9/2003 | Webler et al. | |
| 6,641,189 B2 * | 11/2003 | Moilanen et al. | 294/203 |
| 6,690,963 B2 | 2/2004 | Ben-Haim et al. | |
| 6,718,196 B1 | 4/2004 | Mah et al. | |
| 6,726,638 B2 | 4/2004 | Ombrellaro | |
| 6,730,021 B2 | 5/2004 | Vassiliades, Jr. et al. | |
| 6,758,676 B2 | 7/2004 | Eggert et al. | |
| 6,770,081 B1 * | 8/2004 | Cooper et al. | 606/130 |
| 6,810,281 B2 | 10/2004 | Brock et al. | |
| 6,817,973 B2 | 11/2004 | Merril et al. | |
| 6,853,879 B2 * | 2/2005 | Sunaoshi | 700/253 |
| 6,879,880 B2 * | 4/2005 | Nowlin et al. | 700/260 |
| 6,969,384 B2 | 11/2005 | de Juan, Jr. et al. | |
| 7,118,582 B1 | 10/2006 | Wang et al. | |
| 7,122,028 B2 | 10/2006 | Looper et al. | |
| 7,125,403 B2 * | 10/2006 | Julian | A61B 17/00234 606/1 |
| 7,155,316 B2 * | 12/2006 | Sutherland et al. | 700/248 |
| 7,206,627 B2 | 4/2007 | Abovitz et al. | |
| 7,280,863 B2 | 10/2007 | Shachar | |
| 7,300,450 B2 | 11/2007 | Vleugels et al. | |
| 7,366,562 B2 | 4/2008 | Dukesherer et al. | |
| 7,373,219 B2 | 5/2008 | Nowlin et al. | |
| 7,422,139 B2 | 9/2008 | Shelton, IV et al. | |
| 7,604,646 B2 * | 10/2009 | Goldfarb | A61B 17/00234 606/151 |
| 7,608,083 B2 * | 10/2009 | Lee et al. | 606/130 |
| 7,648,514 B1 * | 1/2010 | Nakao | A61B 17/064 227/175.1 |
| 7,811,296 B2 * | 10/2010 | Goldfarb | A61B 17/122 606/151 |
| 7,835,892 B2 | 11/2010 | Butsev et al. | |
| 7,855,712 B2 * | 12/2010 | Powers et al. | 345/156 |
| 7,877,243 B2 | 1/2011 | Olien et al. | |
| 7,899,553 B2 * | 3/2011 | Barker | 607/126 |
| 7,976,552 B2 * | 7/2011 | Suzuki | A61B 17/1285 606/142 |
| 7,992,910 B2 * | 8/2011 | Seibold et al. | 294/116 |
| 8,070,202 B2 * | 12/2011 | Waldorf et al. | 294/116 |
| 8,104,810 B2 * | 1/2012 | Holcomb et al. | 294/192 |
| 8,287,554 B2 * | 10/2012 | Cerier | A61B 17/00234 606/142 |
| 8,409,273 B2 * | 4/2013 | Thornton | A61B 17/00234 606/148 |
| 8,852,216 B2 * | 10/2014 | Cropper | A61B 17/128 606/142 |

(56) References Cited

U.S. PATENT DOCUMENTS

| | | |
|---|---|---|
| 2001/0004700 A1 | 6/2001 | Honeycutt et al. |
| 2001/0020199 A1 | 9/2001 | Bacchi et al. |
| 2002/0038118 A1* | 3/2002 | Shoham .......................... 606/1 |
| 2002/0112547 A1 | 8/2002 | Eltaib et al. |
| 2002/0120254 A1* | 8/2002 | Julian et al. ..................... 606/1 |
| 2002/0168618 A1 | 11/2002 | Anderson et al. |
| 2003/0023250 A1 | 1/2003 | Watschke et al. |
| 2003/0040758 A1* | 2/2003 | Wang et al. ................... 606/130 |
| 2003/0057973 A1 | 3/2003 | Nojima et al. |
| 2003/0065358 A1* | 4/2003 | Frecker et al. ................ 606/205 |
| 2003/0120268 A1* | 6/2003 | Bertolero ................. A61B 1/12 606/32 |
| 2003/0125716 A1* | 7/2003 | Wang et al. ...................... 606/1 |
| 2003/0146898 A1 | 8/2003 | Kawasaki et al. |
| 2003/0195664 A1* | 10/2003 | Nowlin et al. ................. 700/260 |
| 2004/0009459 A1 | 1/2004 | Anderson et al. |
| 2004/0019447 A1 | 1/2004 | Shachar |
| 2004/0059325 A1* | 3/2004 | Swanson ................ A61B 18/14 606/41 |
| 2004/0092979 A1* | 5/2004 | Burbank et al. ............... 606/158 |
| 2004/0106916 A1 | 6/2004 | Quaid et al. |
| 2004/0111183 A1* | 6/2004 | Sutherland et al. .......... 700/245 |
| 2005/0131390 A1* | 6/2005 | Heinrich et al. ................... 606/1 |
| 2005/0223327 A1 | 10/2005 | Cunningham et al. |
| 2005/0245910 A1 | 11/2005 | Wright et al. |
| 2005/0271302 A1 | 12/2005 | Khamene et al. |
| 2006/0064007 A1 | 3/2006 | Comaniciu et al. |
| 2006/0155273 A1* | 7/2006 | Swanson ............ A61B 18/1442 606/51 |
| 2006/0161136 A1* | 7/2006 | Anderson et al. ................ 606/1 |
| 2006/0195080 A1* | 8/2006 | Ebert ................. A61B 18/1442 606/41 |
| 2006/0207978 A1 | 9/2006 | Rizun et al. |
| 2006/0238189 A1* | 10/2006 | Holcomb et al. ......... 324/207.16 |
| 2006/0279534 A1* | 12/2006 | Powers et al. ................. 345/156 |
| 2006/0293643 A1 | 12/2006 | Wallace et al. |
| 2007/0013336 A1* | 1/2007 | Nowlin et al. ........... 318/568.21 |
| 2007/0032906 A1* | 2/2007 | Sutherland et al. ........... 700/248 |
| 2007/0078484 A1* | 4/2007 | Talarico et al. ................ 606/205 |
| 2007/0112284 A1 | 5/2007 | Hoffman et al. |
| 2007/0135735 A1 | 6/2007 | Ellis et al. |
| 2007/0142749 A1 | 6/2007 | Khatib et al. |
| 2007/0299427 A1* | 12/2007 | Yeung et al. ...................... 606/1 |
| 2008/0027279 A1* | 1/2008 | Abou El Kheir ............. 600/111 |
| 2008/0046122 A1* | 2/2008 | Manzo et al. ................. 700/245 |
| 2008/0086120 A1 | 4/2008 | Mirza et al. |
| 2008/0101895 A1* | 5/2008 | Holcomb et al. ......... 414/226.02 |
| 2008/0117166 A1 | 5/2008 | Rosenberg |
| 2008/0147090 A1* | 6/2008 | Seibold et al. ................ 606/130 |
| 2008/0167662 A1 | 7/2008 | Kurtz |
| 2008/0283577 A1* | 11/2008 | Boyden et al. ............. 227/181.1 |
| 2009/0088775 A1* | 4/2009 | Swarup et al. ................ 606/130 |
| 2009/0171373 A1* | 7/2009 | Farritor et al. ................ 606/130 |
| 2010/0286791 A1* | 11/2010 | Goldsmith ................... 623/23.7 |
| 2011/0009899 A1* | 1/2011 | Picha Muthu et al. ........ 606/207 |
| 2011/0118748 A1* | 5/2011 | Itkowitz ........................ 606/130 |

FOREIGN PATENT DOCUMENTS

| | | |
|---|---|---|
| EP | 1 387 144 | 2/2004 |
| GB | 2 429 254 | 2/2007 |
| JP | H04-332544 | 11/1992 |
| JP | H07-171154 | 7/1995 |
| JP | 2002-336247 | 11/2002 |
| JP | 2003-061956 | 3/2003 |
| JP | 2003-067784 | 3/2003 |
| JP | 2003-319939 | 11/2003 |
| JP | 2004-070669 | 3/2004 |
| JP | 2004-070670 | 3/2004 |
| JP | 2004-159781 | 6/2004 |
| JP | 2004-171251 | 6/2004 |
| WO | WO 99/38141 | 7/1999 |
| WO | WO 02/094080 | 11/2002 |
| WO | WO 03/009212 A1 | 1/2003 |
| WO | WO 2005/110304 | 11/2005 |

OTHER PUBLICATIONS

Patent Cooperation Treaty, International Search Report, International Application No. PCT/US2009/055488, mailed Mar. 2, 2010.
Patent Cooperation Treaty, International Search Report, International Application No. PCT/US2008/072194, mailed Dec. 18, 2008.
Bates, Lisa M. et al., "A Method for Ultrasound Image Based Correction of Intraoperative Brain Shift," Proc. SPIE Medical Imaging 2000; Image Display and Visualization 3976: pp. 58-68.
Bro-Nielsen, Morten, "Finite Element Modeling in Surgery Simulation," Proceedings of The IEEE, vol. 86, No. 3, Mar. 1998, pp. 490-503.
Chen, Hongsheng et al., "Fast Voxelization of Three-Dimensional Synthetic Objects," Journal of Graphics Tools, vol. 3, No. 4, 1998, pp. 33-45.
Freidlin Raisa Z. et al., "NIHmagic: 3D Visualization, Registration and Segmentation Tool," 28th AIPR Workshop: 3D Visualization for Data Exploration and Decision Making, Proc. of SPIE vol. 3905, 2000, pp. 8 pages.
Hesina, Gerd et al., "Distributed Open Inventor: A Practical Approach to Distributed 3D Graphics," Vienna University of Technology, Austria, 1999, pp. 74-81.
Iwata, Hiroo et al., "Volume Haptization", Institute of Engineering Mechanics, 1993, pp. 16-23.
Kreeger, Kevin et al., "Mixing Translucent Polygons with Volumes," Dept. of Computer Science, SUNY at Stony Brook, 1999, pp. 191-199.
Minsky, Margaret et al., "Feeling and Seeing: Issues in Force Display," Dept of Computer Science, 1990, pp. 235-242, 270.
Stanley, Michael C. et al., "Computer Simulation of Interacting Dynamic Mechanical Systems Using Distributed Memory Parallel Processors," DSC-vol. 42, Advances in Robotics, ASME 1992, pp. 55-61.
Su, S. Augustine et al., "The Virtual Panel Architecture: A 3D Gesture Framework," Computer Science Department, 1993, pp. 387-393.
Weiler, Manfred et al., "Direct Volume Rendering in OpenSG," Computers & Graphics 28,2004, pp. 93-98.
Weiskopf, Daniel et al., "Volume Clipping via Per-Fragment Operations in Texture-Based Volume Visualization," Visualization and Interactive Systems Group, 2002, pp. 93-100.
Westermann, Rudiger et al., "Efficiently Using Graphics Hardware in Volume Rendering Applications," Computer Graphics Proceedings, Annual Conference Series, 1998, pp. 169-177.
Yamakita, M. et al., "Tele Virtual Reality of Dynamic Mechanical Model," Proceedings of the 1992 IEEE/RSJ International Conference on Intelligent Robots and Systems, Jul. 7-10, 1992, pp. 1103-1110.
Alger et al., "Real-Time Ultrasound Imaging Simulation," 1998, 24 pages.
Cotin et al. "Real-Time Elastic Deformations of Soft Tissues for Surgery Simulation", IEEE Transactions of Visualization and Computer Graphics, vol. 5, No. 1, Jan.-Mar. 1999, pp. 62-73.
Ehricke, Hans-Heino, "SONOSim3D: A Multimedia System for Sonography Simulation and Education with an Extensible Case Database", European Journal of Ultrasound 7, 1998, pp. 225-230.
International Preliminary Report on Patentability, International Application No. PCT/US2005/031391, dated Apr. 3, 2007.
Japanese Patent Office, Notice for Reasons of Rejection, Application No. 2007-533500, dated May 11, 2010.
Maul et al. "Ultrasound Simulators: Experience with the SonoTrainer and Comparative Review of Other Training Systems", Ultrasound Obstet Gynecol, Aug. 4, 2004, pp. 581-585.
Office Action by UK Intellectual Property Office, Application No. GB0706763, dated Jul. 1, 2010.
Written Opinion of the International Searching Authority, Application No. PCT/US2005/031391, dated Mar. 1, 2006.

(56) References Cited

OTHER PUBLICATIONS

United States Patent and Trademark Office, Office Action, U.S. Appl. No. 10/950,766 mailed Dec. 28, 2007.
United States Patent and Trademark Office, Office Action, U.S. Appl. No. 10/950,766 mailed Jun. 28, 2007.
United States Patent and Trademark Office, Office Action, U.S. Appl. No. 10/950,766 mailed Aug. 11, 2008.
United States Patent and Trademark Office, Office Action, U.S. Appl. No. 10/950,766 mailed Feb. 2, 2009.
United States Patent and Trademark Office, Office Action, U.S. Appl. No. 10/950,766 mailed Jul. 13, 2009.
United States Patent and Trademark Office, Office Action, U.S. Appl. No. 12/946,551 mailed Jan. 24, 2012.
United States Patent and Trademark Office, Office Action, U.S. Appl. No. 12/946,551 mailed Jul. 18, 2011.
Patent Cooperation Treaty, International Preliminary Report on Patentability, International Application No. PCT/US2009/055488, mailed Mar. 24, 2011.
Bethea, B. et al., Application of Haptic Feedback to Robotic Surgery, Laparoendosc Adv Surg Tech A. Author manuscript; available in PMC Nov. 14, 2005. Published in final edited form as: J Laparoendosc Adv Surg Tech A., 2004, 14(3): 191-195.
Bholat et al., Tactile Feedback is Present during Minimally Invasive Surgery, J Am Coll Surg., 1999, 189(4):349-55.
Hannaford et al., Computerized Endoscopic Surgical Grasper, Proceedings, Medicine Meets Virtual Reality, San Diego, CA, 1998.
Hu et al., Real-Time Haptic Feedback in Laparoscopic Tools for Use in Gastro-Intestinal Surgery, MICCAI, 2002, LNCS 2488, pp. 66-74, 2002.
Moy et al., A Compliant Tactile Display for Teletaction, IEEE International Conference on Robotics and Automation, 2000, pp. 3409-3415 vol. 4.
Okamura et al., The Haptic Scissors: Cutting in Virtual Environments, IEEE International Conference on Robotics and Automation, 2003, pp. 828-833 vol. 1.
Schirmbeck et al., Tactile Feedback without Direct Touch: An Achievement for Robotically Working Heart Surgeons? 2005, web page at http:// www6.in.tum.de/Main/Publications/Braun2005a.pdf, as available via the Internet.
Yao et al., A Tactile Enhancement Instrument for Minimally Invasive Surgery, Computer Aided Surgery, 2005, vol. 10, No. 4, pp. 233-239.
Tactile Sensor Acts as a Human Finger in Minimally Invasive Surgery, Phys.org, 2007, web page at http://phys.org/news102155952.html, as available via the Internet.

\* cited by examiner

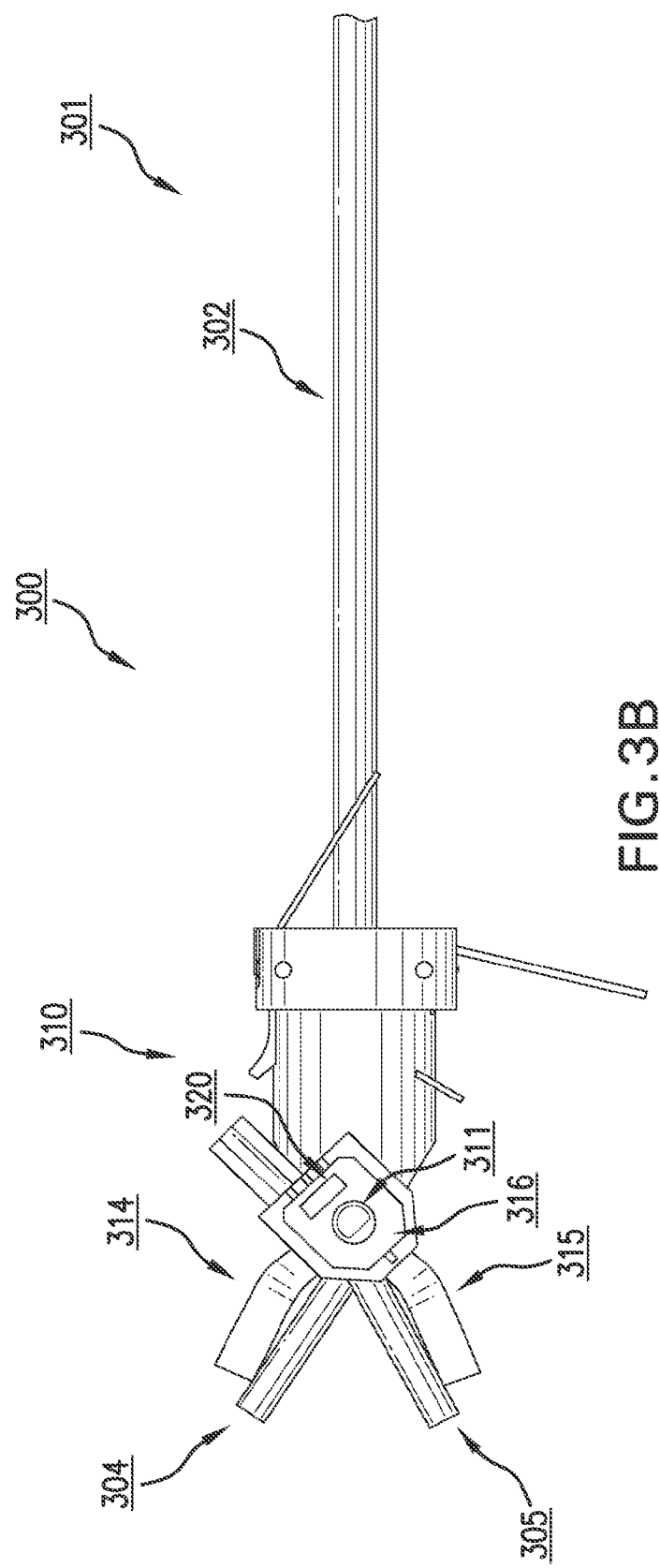

SYSTEMS AND METHODS FOR SENSING HAND MOTION BY MEASURING REMOTE DISPLACEMENT

FIELD OF THE INVENTION

The present invention generally relates to medical devices, and more specifically relates to systems and methods for sensing hand motion by measuring remote displacement.

BACKGROUND

Conventional medical simulations require specialized devices specific to each simulator to simulate a specific medical procedure. Rather than accepting tools designed for and used during actual surgical procedures, certain medical simulators may operate only with tools specifically designed for that medical simulator. Frequently, these simulator-specific tools only approximate the design and feel of real surgical tools, diminishing the realism and effectiveness of the medical simulation.

As one example, a medical simulator for laparoscopic surgery may use a laparoscopic tool designed for interaction with the simulator. Such a laparoscopic simulation tool may only approximate the design and operation of real laparoscopic tools. Laparoscopic surgery is performed by using tools where the action is delivered at a distance through a mechanical linkage. Thus, a need exists for systems and methods for sensing hand motion by measuring remote displacement.

SUMMARY

Embodiments of the present invention provide systems and methods for sensing hand motion by measuring remote displacement. In one embodiment, a system for sensing hand motion by measuring remote displacement comprises an apparatus comprising a first surface configured to engage a first distal member of a surgical tool, a second surface configured to engage a second distal member of the surgical tool, the second surface coupled to the first surface at a pivot point; and a sensor configured to detect a relative movement of the first surface and the second surface about the pivot point and to generate a signal corresponding to the relative movement.

In another embodiment, a method for sensing hand motion by measuring remote displacement comprises engaging a first distal member of a surgical tool at a first surface, engaging a second distal member of the laparoscopic tool at a second surface, the second surface coupled to the first surface at a pivot point; determining a relative movement of the first distal member and the second distal member; and outputting a signal based at least in part on the relative movement of the first distal member and the second distal member.

These illustrative embodiments are mentioned not to limit or define the invention, but to provide two examples to aid understanding thereof. Illustrative embodiments are discussed in the Detailed Description, and further description of the invention is provided there. Advantages offered by the various embodiments of the present invention may be further understood by examining this specification.

BRIEF DESCRIPTION OF THE DRAWINGS

These and other features, aspects, and advantages of the present invention are better understood when the following Detailed Description is read with reference to the accompanying drawings, wherein:

FIGS. 3A and 3B are side perspectives of an illustration of a system for sensing hand motion by measuring remote displacement according to one embodiment of the present invention;

DETAILED DESCRIPTION

Figure 1:
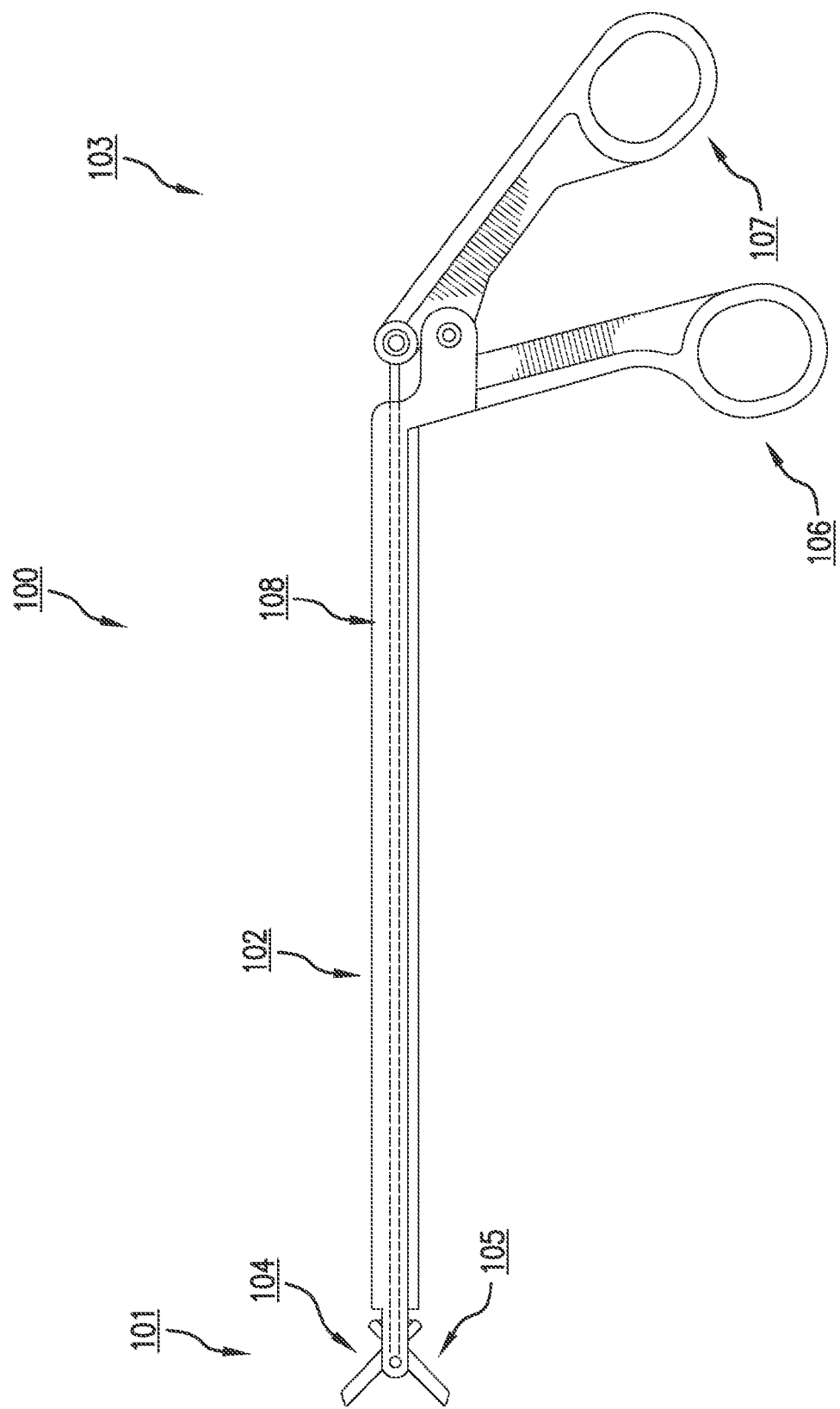
FIG. 1 is an illustration of a surgical tool used for sensing hand motion by measuring remote displacement according to one embodiment of the present invention.

Embodiments of the present invention comprise systems and methods for sensing hand motion by measuring remote displacement. Systems according to the present invention may be embodied in a number of ways. Certain embodiments of the present invention may, for example, sense the motion of a laparoscopic tool through two members attached to a pivot point.

Example of a System for Sensing Hand Motion by Measuring Remote Displacement In one illustrative embodiment of the present invention, a system such as a medical procedure simulator comprises an apparatus configured to engage a surgical tool, such as a laparoscopic tool. In the embodiment, the laparoscopic tool comprises a pair of handles or holds. The handles, at the proximal end of the laparoscopic tool, are connected to a distal end of the tool via a thin shaft. The handles are configured to manipulate a pair of members, such as scissor blades or prongs located at the distal end of the laparoscopic tool. By engaging the handle of the laparoscopic tool a user may open and/or close the first distal member and the second distal member of the tool.

The apparatus is engaged with the laparoscopic tool by sliding the apparatus over the tool's distal end. An anchor secures the apparatus about the laparoscopic tool. The anchor comprises two spring loaded members. Each spring loaded member applies pressure about the shaft of the laparoscopic tool to keep the apparatus in place. The anchor can be configured to accept a plurality of tools, for example, by being tolerant of various diameters of laparoscopic tool shafts.

A first surface of the apparatus is configured to engage the first distal member of the laparoscopic tool, and a second surface of the apparatus is configured to engage the second distal member of the laparoscopic tool. The surfaces may engage the distal members through several means, such as through direct contact, or through an interlocking mechanism. The first surface of the apparatus and the second surface of the apparatus are coupled together at a pivot point. During operation of the laparoscopic tool, the distal members open and/or close, causing the surfaces of the apparatus to flex or contract in parallel with the distal members. The apparatus can be configured to engage a laparoscopic tool with asymmetric operation. In such an embodiment, the first surface and the second surface of the apparatus can be configured to move independently of each other, or asymmetrically. In another variation, the apparatus can be configured to engage a laparoscopic tool with symmetric operation. During symmetric operation, the first surface of the apparatus and the second surface of the apparatus may be displaced or move in unison towards or away from each other.

As the laparoscopic tool's distal members open and close, the first and second surfaces of the apparatus operate in a corresponding fashion. As the first and second surfaces open and close, one or more sensors detect the relative movement of the surfaces about the pivot point. The sensor(s) can report the relative movement of the surfaces to a processor and/or a surgical simulation device. By providing systems and methods which can be configured to accept a variety of different types and brands of surgical tools, systems and methods of the present invention may provide a more realistic surgical simulation.

This example is given to introduce the reader to the general subject matter discussed herein. The disclosure is not limited to this example. Further details regarding various embodiments for sensing hand motion by measuring remote displacement are described below Example of a Surgical Tool FIG. 1 is an illustration of a surgical tool used for sensing hand motion by measuring remote displacement according to one embodiment of the present invention. According to the illustration shown in FIG. 1, a surgical tool used for sensing hand motion by measuring remote displacement comprises a laparoscopic tool 100. Laparoscopic tools, such as the one illustrated in FIG. 1, may be used to create incisions or grasp objects during a surgical procedure. The laparoscopic tool 100 comprises a distal end 101, a proximal end 103, and a shaft 102 connecting the distal end 101 with the proximal end 103. In other embodiments, the surgical tool used for sensing hand motion by measuring remote displacement comprises a gynecological tool, an arthroscopic tool, a surgical knife, scissors, tweezers, clamps, retractors, distractors, forceps, calipers, a surgical elevator, or a surgical suture. The surgical tool may comprise a real surgical tool, or a proxy/substitute surgical tool, which is intended to mimic the look, feel, and/or function of a surgical tool.

At the proximal end 103, the laparoscopic tool 100 comprises a first handle 106 and a second handle 107. The handles 106, 107 may be grasped by a user and manipulated. Alternatively, a robot or mechanical device may operate the laparoscopic tool 100. At the distal end 101, the laparoscopic tool 100 comprises a first distal member 104 and a second distal member 105. Distal members 104, 105 may each comprise a blade, for example, to make a surgical incision. Alternatively, distal members 104, 105 may each comprise a grasper or a gripper. A linkage 108 extends through the shaft 102 from the proximal end 103 to the distal end 101, and mechanically connects the handles 106, 107 with the distal members 104, 105.

By manipulating the handles 106, 107, the first distal member 104 and/or the second distal member 105 may be operated. For example, compressing or flexing the second handle 107 towards the first handle 106 may cause the first distal member 104 and the second distal member 105 to compress or pivot towards each other. Releasing or opening the handles 106, 107 may cause the distal members 104, 105 to open, or pivot away from each other.

In some embodiments, the distal members 104, 105 of the laparoscopic tool 100 may operate symmetrically. That is, as the handles 106, 107 are manipulated, each distal member 104, 105 moves an equal amount. In other embodiments, the distal members 104, 104 operate asymmetrically. In one example, as the handles 106, 107 are manipulated, the first distal member 104 remains in place while the second distal member 105 moves towards or away from the first distal member 104. Movement of one or both of the handles 106, 107 may directly correspond to movement of one or both of the distal members 104, 105.

Examples of Systems for Sensing Hand Motion by Measuring Remote Displacement

Figure 2:
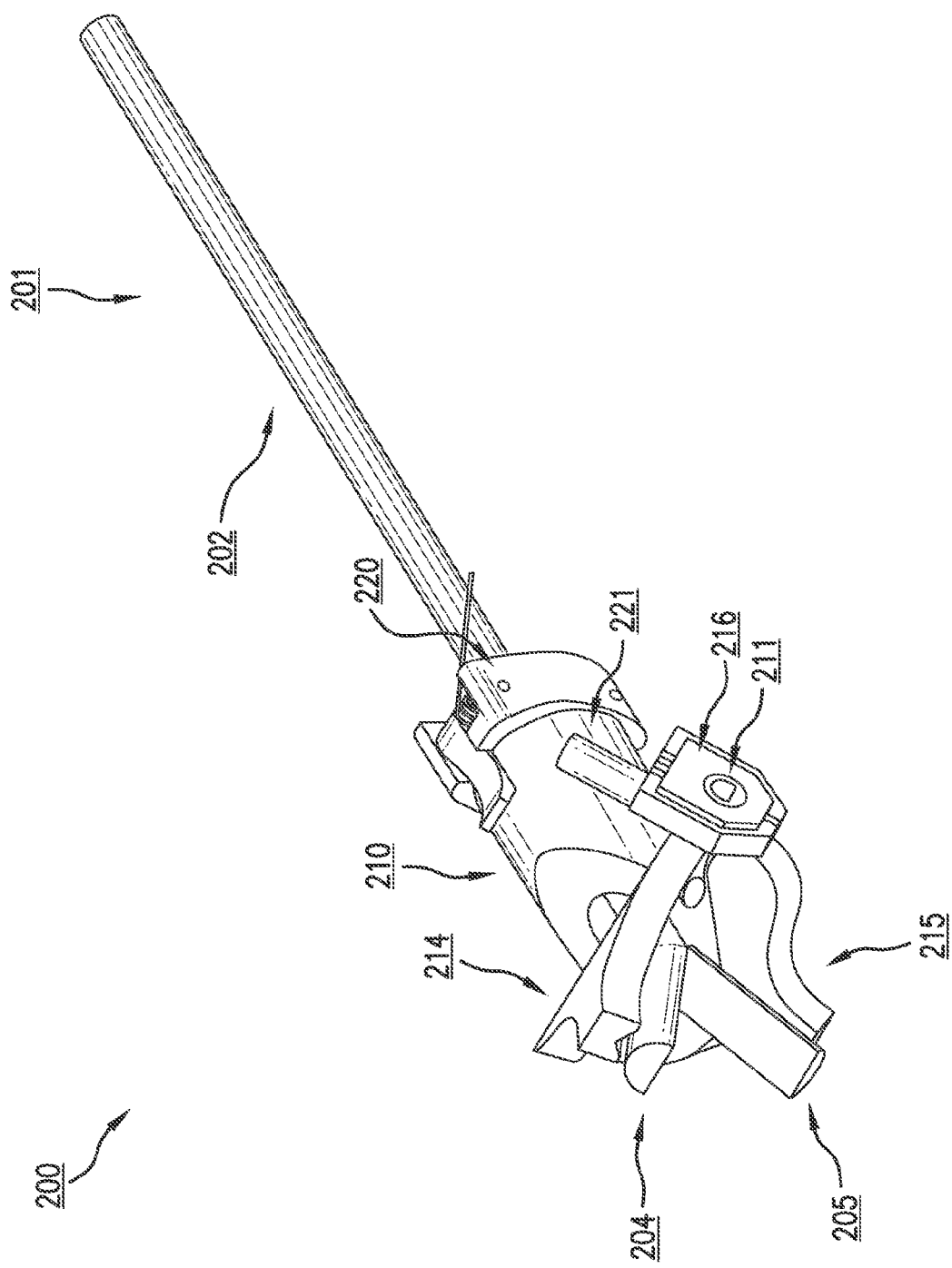
FIG. 2 is a top perspective of an illustration of a system for sensing hand motion by measuring remote displacement according to one embodiment of the present invention.

FIG. 2 is a top perspective of an illustration of a system for sensing hand motion by measuring remote displacement according to one embodiment of the present invention. According to the illustration in FIG. 2, the system 200 comprises an apparatus 210 fitted about a surgical tool 201. The surgical tool 201 comprises a laparoscopic tool, such as the one illustrated in FIG. 1. In other embodiments, different surgical tools 201 may be used.

As illustrated in FIG. 2, the surgical tool 201 comprises a first distal member 204 and a second distal member 205. A shaft 202 connects the distal members 204, 205 with a control mechanism (not shown in FIG. 2). The control mechanism may comprise a pair of handles, such as the handles 106, 107 illustrated in FIG. 1. In other variations, the surgical tool 201 may be manipulated by other means.

The apparatus 210 is fitted about the distal end of the surgical tool 201. In one embodiment, the entire apparatus assembly may measure approximately 3 centimeters in length. In other variations, the apparatus may be longer or shorter. The apparatus 210 can be configured to minimally restrict or impede the motion or operation of the surgical tool 201. By restricting or minimizing the chance in operation of the surgical tool, users of the surgical tool equipped with the apparatus may be more immersed in a medical simulation, as the apparatus would be less noticeable to the user. As one example, the apparatus 210 may be constructed, at least in part, of a lightweight plastic or resin material. An apparatus 210 constructed of a heavyweight material may change or impede the operation of the surgical tool 201, for example, by impeding the motion of the distal members 204, 205. In contrast, an apparatus 210 constructed of lightweight materials may not impede the operation of the surgical tool, thereby increasing the effectiveness of the surgical simulation.

The apparatus 210 comprises an anchor 220 configured to fit about the shaft 202 of the surgical tool 201, and configured to secure the apparatus 210 about the shaft 202. As an example, the anchor 220 may be configured to slide over the distal end of the surgical tool 201, as the distal members 204, 205, are contracted together. In one embodiment, the anchor 220 comprises a first anchoring surface and a second anchoring surface (not shown in FIG. 2). In another embodiment, the anchor 220 may comprise a plurality of anchoring surfaces. For example, the anchor 220 may comprise an iris mechanism comprising a plurality of anchoring surfaces. Each anchoring surface can be spring loaded, and configured to apply pressure to the shaft 202 of the surgical tool 201 to secure the apparatus 210 about the shaft 201.

Each anchoring surface may be spring loaded. By spring-loaded the anchoring surfaces, the anchoring surfaces may be better able to hold the shaft in place. In another variation, the anchoring surfaces may secure the apparatus 210 about the surgical tool 201 through other means. For example, the anchoring surfaces may comprise a material resistant to flexure. When the shaft 202 is inserted through the anchor 220, the anchoring surfaces may naturally resist flexure.

The anchor 220 may be configured to accept a variety of different surgical tools. In one embodiment, the anchoring surfaces are configured to accept a range of diameters of surgical tools. By being tolerant of various diameters of surgical tools, a surgical simulator utilizing the apparatus 210 may be more accommodating and practical.

The apparatus 210 additionally comprises a first surface 214 and a second surface 215. The surfaces may comprise a flat, rigid material, such as plastic or metal. The first surface 214 and the second surface 215 can be affixed to a pivot point 211. By affixing the surfaces 214, 215 to the pivot point 211, the surfaces may move or pivot about the pivot point 211.

The first surface 214 can be configured to engage the first distal member 204 of the surgical tool 201. Additionally, the second surface 215 can be configured to engage the second distal member 205 of the surgical tool 201. The surfaces 214, 215 of the apparatus 210 may engage the distal members 204, 205 of the surgical tool 201 through direct contact, such as illustrated in FIG. 2. In one variation not illustrated in FIG. 2, one or both of the surfaces 214, 215 may slidably engage the distal members 204, 205 through an open loop (not shown in FIG. 2).

As the surgical tool 201 is manipulated, the distal members 204, 205 may flex or pivot about a pivot point. By engaging the distal members 204, 205, the surfaces 214, 215 of the apparatus may flex or pivot in tandem with the distal members 204, 205. As the surfaces flex or pivot, a sensor 216 may detect relative movements of the surfaces 214, 215. For example, as the surfaces 214, 215 move towards and away from each other, a sensor detects their movement about the pivot point, and generates a signal based at least in part on their movement. In one embodiment, a plurality of sensors 216 detect the relative movements of the surfaces 214, 215. For instance, a first sensor may detect movement of the first surface 214, and a second sensor may detect movement of the second sensor 215. Each of the plurality of sensors may be configured to detect movement of a surface 214, 215 from a ground or rest position.

The surfaces 214, 215 of the apparatus 210 may be configured to engage the surgical tool 201 without impeding the motion of the surgical tool 201. For example, the surfaces 214, 215 may engage the distal members 204, 205 with little or no resistance. Thus, a user operating the surgical tool 201 while it is engaged by the apparatus 210 may experience little or substantially no difference in operation of the surgical tool 201.

The first surface 214 may be configured to move independently of the second surface 215. For example, as the first surface 214 pivots about the pivot point 211, the second surface 215 may remain stationary. A sensor may be configured to detect the asymmetric movement of the first surface 214 relative to the second surface 215, and to generate a signal based at least in part on the asymmetric movement.

The apparatus 210 further comprises a sensor 216. The sensor 216 can be configured to detect a relative movement of the first surface 214 and the second surface 215 about the pivot point 211. In one variation, the sensor is configured to measure the displacement of the surfaces 214, 215 about the pivot point 211. The sensor 216 may comprise a potentiometer. Alternatively, the sensor 216 may comprise an optical sensor, or some other type of sensor configured to detect motion. In one variation, the apparatus 210 comprises two sensors, each sensor configured to detect a relative movement of a surface. In another variation, the apparatus 210 comprises a plurality of sensors.

The sensor 216 may be configured to communicate with a processor and/or a simulation device such as a surgical simulator (not shown in FIG. 2). In one embodiment, the sensor 216 generates a signal based at least in part on the relative movement of the first surface 214 and the second surface 215. A processor configured to receive one or more signals from the sensor(s) may be configured to process the sensor signals to determine a displacement of the surfaces.

The sensor 216 may send the signal to a simulation device through a connecting mechanism 221. Connecting mechanism 221 may comprise, for example, a wire capable of transmitting signals. In another variation, the sensor 216 may communicate with a processor or medical simulator through a wireless connecting mechanism 221. The processor may be configured to receive signals from the sensor based at least in part on the relative movement of the first surface 204 and the second surface 205 about the pivot point 211.

The apparatus 210 may further comprise one or more actuators (not shown in FIG. 2) configured to provide vibrotactile feedback to the surgical tool 201. The actuators may be in communication with a processor or a simulation device, such as a laparoscopic surgical simulator. As the sensor 216 detects relative movement of the first surface 214 and the second surface 215, the simulation device may transmit an actuator signal to the actuator. The actuator signal may cause one or more actuators to provide vibrotactile feedback to the surgical tool 201.

Figure 3A:
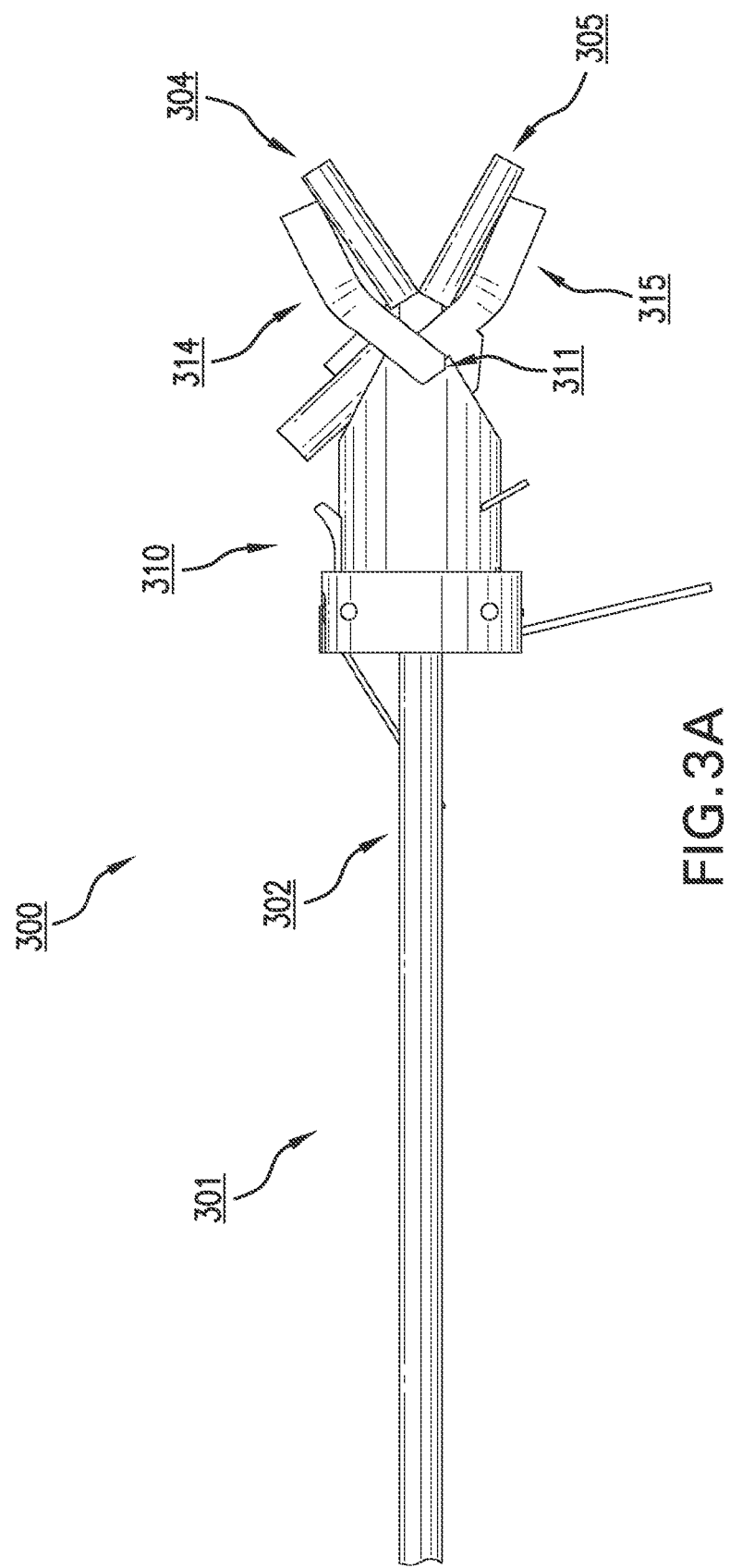

FIGS. 3A and 3B are side perspectives of an illustration of a system for sensing hand motion by measuring remote displacement according to one embodiment of the present invention. FIG. 3A illustrates one side perspective of a system for sensing hand motion by measuring remote displacement. FIG. 3B illustrates the opposite side perspective of the system for sensing hand motion by measuring remote displacement.

According to the illustrations in FIG. 3A and FIG. 3B, the system 300 comprises an apparatus 310 fitted about a surgical tool 301. The surgical tool comprises a first distal member 304 and a second distal member 305. A shaft 302 connects the distal members 304, 305 with a control mechanism, such as a pair of handles (not shown in FIGS. 3A, 3B).

The apparatus 310 for measuring remote displacement comprises a first surface 314 and a second surface 315. As shown in FIGS. 3A and 3B, the first surface 314 is engaging the first distal member 304, and the second surface 315 is engaging the second distal member 305. As shown in FIGS.

3A and 3B, the surfaces 314, 315 engage the distal members 304, 305 through direct contact. One or more spring mechanisms (not shown in FIGS. 3A and 3B) may apply pressure on one or both surfaces 314, 315 for reliably engaging the distal members 304, 305.

As shown in FIG. 3B, the apparatus 310 comprises a sensor 316. The sensor 316 is configured to detect a relative movement of the first surface 314 and the second surface 315 about the pivot point 311. The sensor 316 is also configured to generate a signal based at least in part on the relative movement of the first surface 314 and the second surface 315.

The sensor 316 is in communication with a processor 320. The processor is configured to receive a signal from the sensor. For example, the processor can be configured to receive signals from the sensor indicating relative movement of the surfaces 314, 315 about the pivot point. The processor may be in communication with a medical simulator (not shown in FIGS. 3A and 3B).

Figure 4:
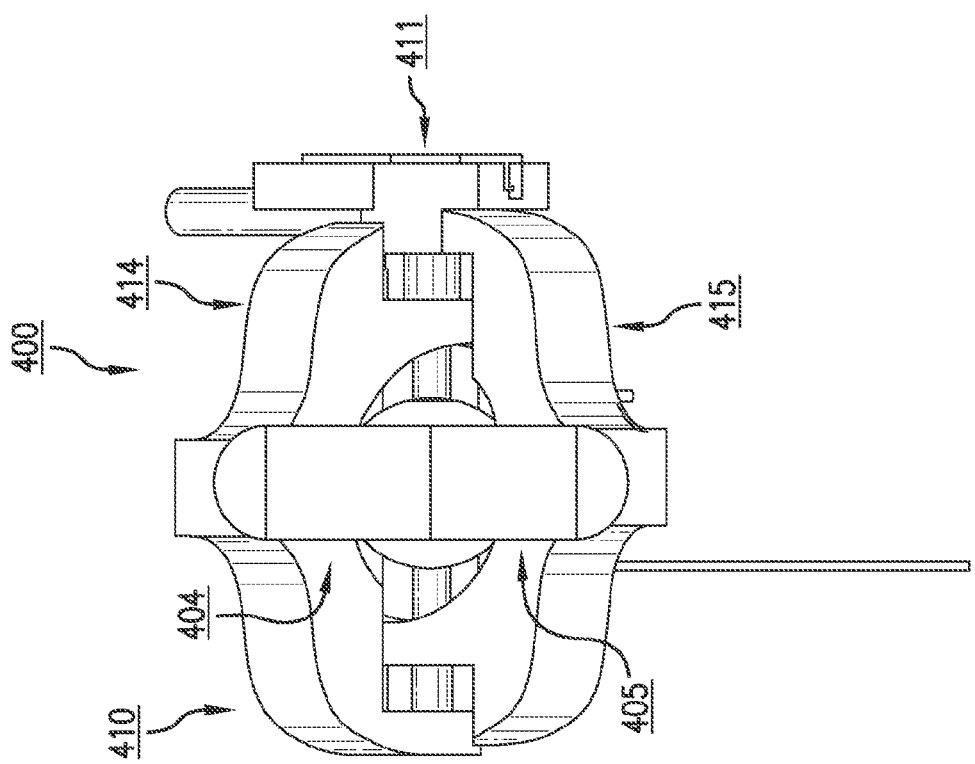
FIG. 4 is a front perspective of an illustration of a system for sensing hand motion by measuring remote displacement according to one embodiment of the present invention.

FIG. 4 is a front perspective of an illustration of a system for sensing hand motion by measuring remote displacement according to one embodiment of the present invention. According to the illustration in FIG. 4, the system 400 comprises an apparatus 410 for measuring remote displacement. The apparatus 410 is fitted about a surgical tool. As shown in FIG. 4, the surgical tool comprises a first distal member 404 and a second distal member 405. A shaft (not shown) connects the distal members 404, 405 with a control mechanism, such as a pair of handles (not shown in FIG. 4). A user may manipulate the control mechanism, causing the distal members 404, 405 to expand and contract, or move towards or away from each other, respectively. As shown in FIG. 4, the distal members 404, 405 are shown expanded, away from each other.

The apparatus 410 for measuring remote displacement comprises a first surface 414 and a second surface 415. The second surface 415 is coupled to the first surface 414 at a pivot point 411. As shown in FIG. 4, the first surface 414 is engaging the first distal member 404, and the second surface 415 is engaging the second distal member 405. In the embodiment shown in FIG. 4, the surfaces 414, 415 are engaging the distal members 404, 405 through direct contact. One or more spring mechanisms (not shown in FIG. 4) may apply pressure on one or both surfaces 414, 415 for reliably engaging the distal members 404, 405.

Figure 5:
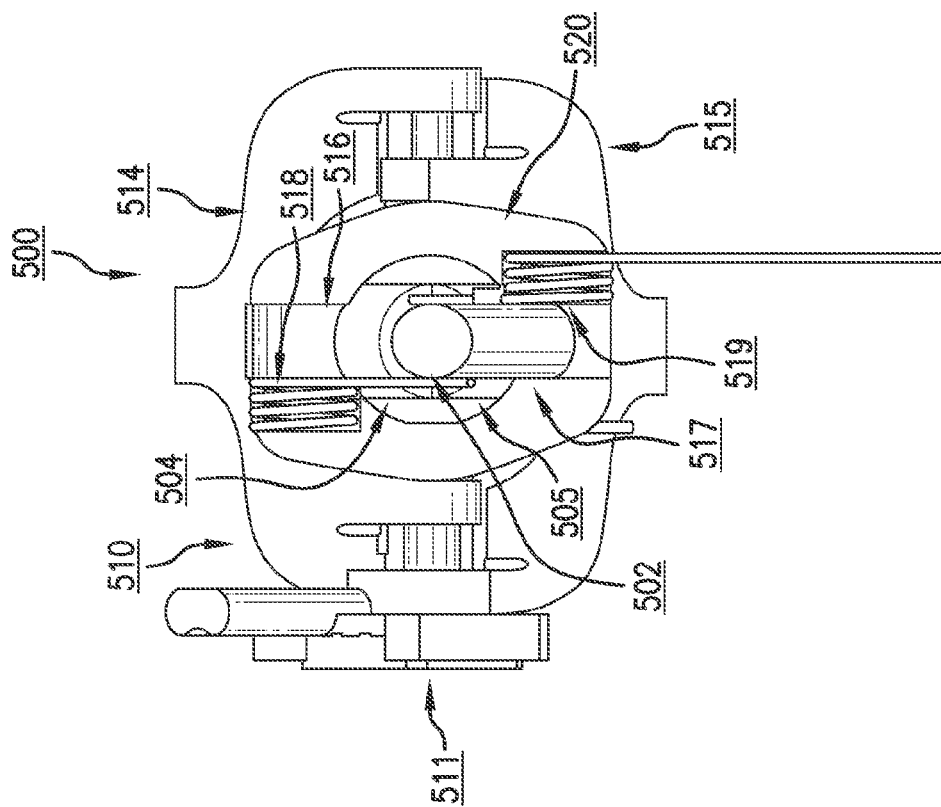
FIG. 5 is a rear perspective of an illustration of a system for sensing hand motion by measuring remote displacement according to one embodiment of the present invention.

FIG. 5 is a rear perspective of an illustration of a system for sensing hand motion by measuring remote displacement according to one embodiment of the present invention. According to the illustration in FIG. 5, the system 500 comprises an apparatus for measuring remote displacement 510. The apparatus 510 is fitted about a surgical tool. As shown in FIG. 5, the surgical tool comprises a first distal member 504 and a second distal member 505. A shaft 502 connects the distal members 504, 505 with a control mechanism, such as a pair of handles (not shown in FIG. 5). A user may manipulate the control mechanism, causing the distal members 504, 505 to expand and contract, or move towards or away from each other, respectively. The apparatus 510 comprises a first surface 514 and a second surface 515. The second surface 515 is coupled to the first surface 514 at a pivot point 511. As shown in FIG. 5, the first surface 514 is engaging the first distal member 504, and the second surface 515 is engaging the second distal member 505.

The apparatus 510 additionally comprises an anchor 520 fitted about the surgical tool. The anchor 520 can fit about the surgical tool by sliding over the distal end of the surgical tool. The anchor 520 is configured to secure the apparatus 510 about the surgical tool.

The anchor 520 comprises a first anchoring surface 516 and a second anchoring surface 517. In other embodiments, the anchor 520 may comprise a plurality of anchoring surfaces. As shown in FIG. 5, each of the anchoring surfaces 516, 517 are spring loaded. The first anchoring surface 516 is engaged by a first spring 518, and the second anchoring surface 517 is engaged by a second spring 519. Each spring loaded anchoring surface 516, 517 applies pressure about the shaft 502 of the surgical tool to keep the apparatus 510 in place. The anchor 520 can be configured to accept a plurality of tools, for example, by being tolerant of various diameters of laparoscopic tool shafts. In one variation, the anchoring members 516, 517 flexibly engage a plurality of surgical tools, each surgical tool having a different diameter.

Figure 6:
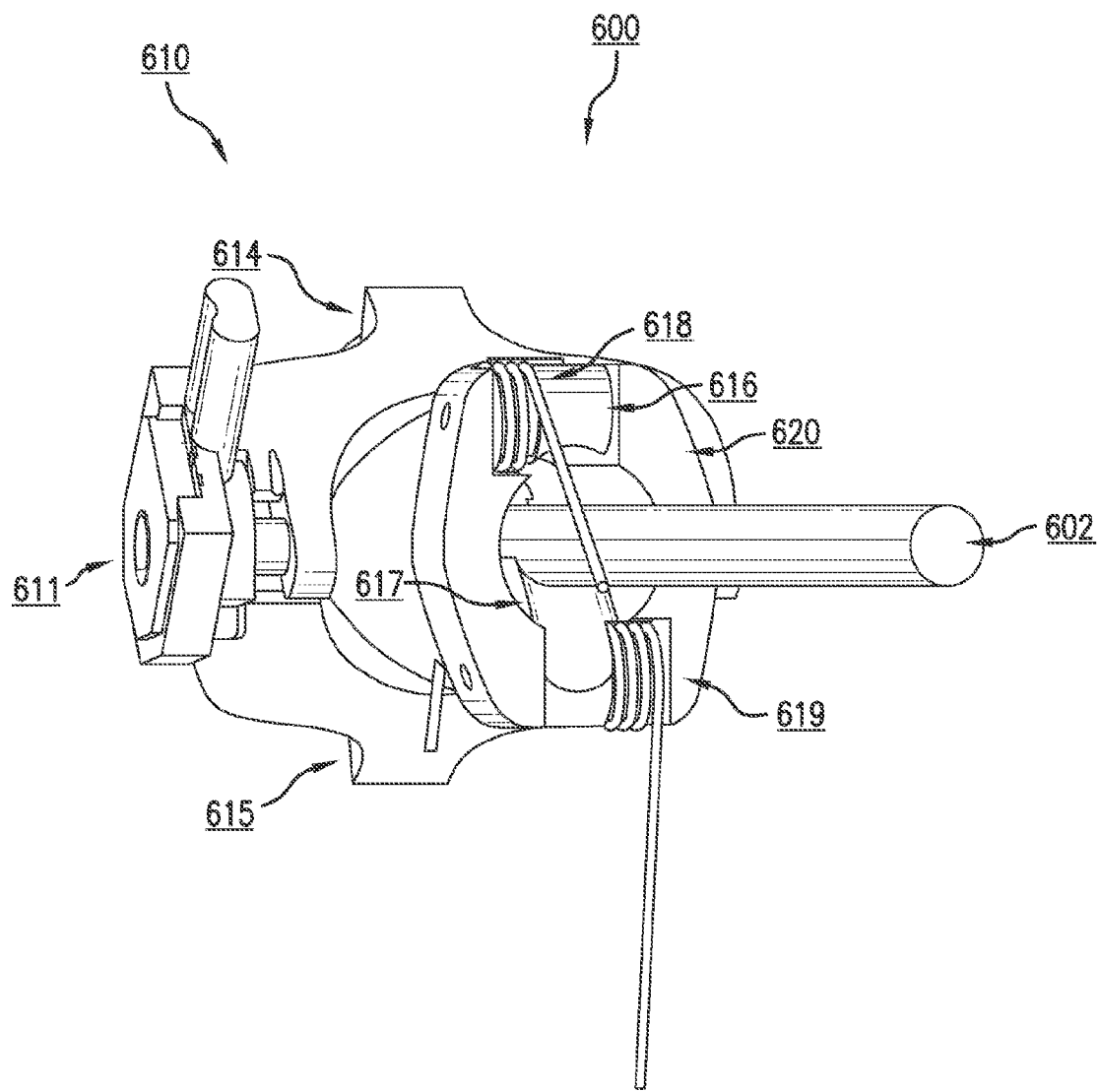
FIG. 6 is a side-rear perspective of an illustration of a system for sensing hand motion by measuring remote displacement according to one embodiment of the present invention.

FIG. 6 is a side-rear perspective of an illustration of a system for sensing hand motion by measuring remote displacement according to one embodiment of the present invention. According to the illustration in FIG. 6, the system 600 comprises an apparatus for measuring remote displacement 610. The apparatus 610 is fitted about the shaft 602 of a surgical tool. The apparatus 610 comprises a first surface 614 and a second surface 615. The second surface 615 is coupled to the first surface 614 at a pivot point 611. Each of the surfaces 614, 615 engages a distal member (not shown in FIG. 6) of the surgical tool.

The apparatus 610 additionally comprises an anchor 620 fitted about the surgical tool. The anchor 620 can fit about the surgical tool by sliding over the distal end of the surgical tool. The anchor 620 is configured to secure the apparatus 610 about the surgical tool.

The anchor 620 comprises a first anchoring surface 616 and a second anchoring surface 617. As shown in FIG. 6, each of the anchoring surfaces 616, 617 are spring loaded. The first anchoring surface 616 is engaged by a first spring 618, and the second anchoring surface 617 is engaged by a second spring 619. Each spring loaded anchoring surface 616, 617 applies pressure about the shaft 602 of the surgical tool to keep the apparatus 610 in place.

Figure 7:
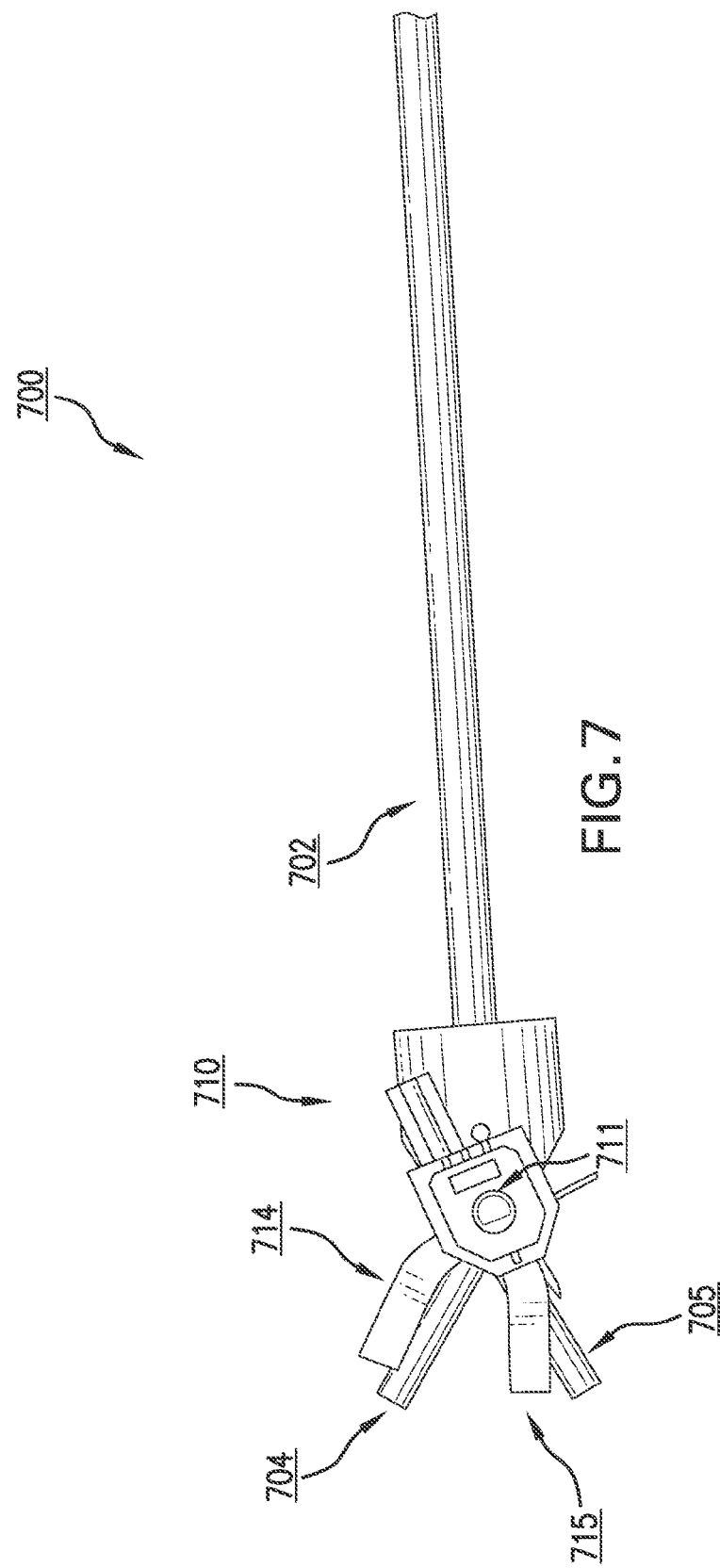
FIG. 7 is a side perspective of an illustration of a system for sensing hand motion by measuring remote displacement according to one embodiment of the present invention.

FIG. 7 is a side perspective of an illustration of a system for sensing hand motion by measuring remote displacement according to one embodiment of the present invention. According to the illustration in FIG. 7, the system 700 comprises an apparatus 710 fitted about the distal end and shaft 702 of a surgical tool. The surgical tool further comprises a first distal member 704 and a second distal member 705. The shaft 702 connects the distal members 704, 705 with a control mechanism, such as a pair of handles (not shown in FIG. 7).

The apparatus 710 for measuring remote displacement comprises a first surface 714 and a second surface 715. The second surface 715 is coupled to the first surface 714 at a pivot point 711. Each of the surfaces 714, 715 engages one of the distal members 704, 705. As shown in FIG. 7, the first surface 714 is engaging the first distal member 704 through direct contact. In contrast, the second surface 715 is slidably engaging the second distal member 705. For example, the second distal member 705 may slide through a loop or gap in the second surface 715, such that when the second distal member 705 moves, the second surface 715 moves in a corresponding fashion.

Figure 8:
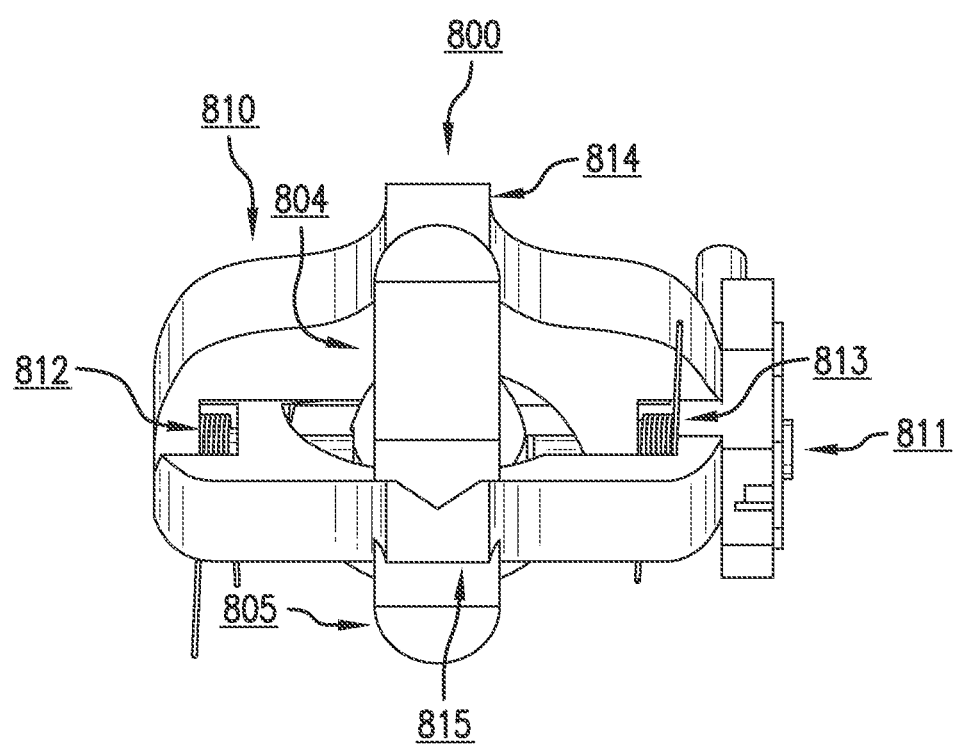
FIG. 8 is front perspective of an illustration of a system for sensing hand motion by measuring remote displacement according to one embodiment of the present invention.

FIG. 8 is a front perspective of an illustration of a system for sensing hand motion by measuring remote displacement according to one embodiment of the present invention. According to the illustration in FIG. 8, the system 800 comprises an apparatus 810 fitted about the distal end of a surgical tool. The surgical tool comprises a first distal member 804 and a second distal member 805. A shaft (not shown in FIG. 8) of the surgical tool connects the distal members 804, 805 with a control mechanism, such as a pair of handles (not shown in FIG. 8).

The apparatus 810 for measuring remote displacement comprises a first surface 814 and a second surface 815. The second surface 815 is coupled to the first surface 814 at a pivot point 811. Each of the surfaces 814, 815 engages one of the distal members 804, 805. As shown in FIG. 8, the first surface 814 is engaging the first distal member 804 through direct contact. In contrast, the second surface 815 is slidably engaging the second distal member 805. One or more spring mechanisms 812 and 813 may apply pressure on one or both surfaces 814, 815 for reliably engaging the distal members 804, 805. In the illustration, the second distal member 805 is fitted through a gap in the second surface 815, such that when the second distal member 805 moves, the second surface 815 moves in a corresponding fashion.

Figure 9:
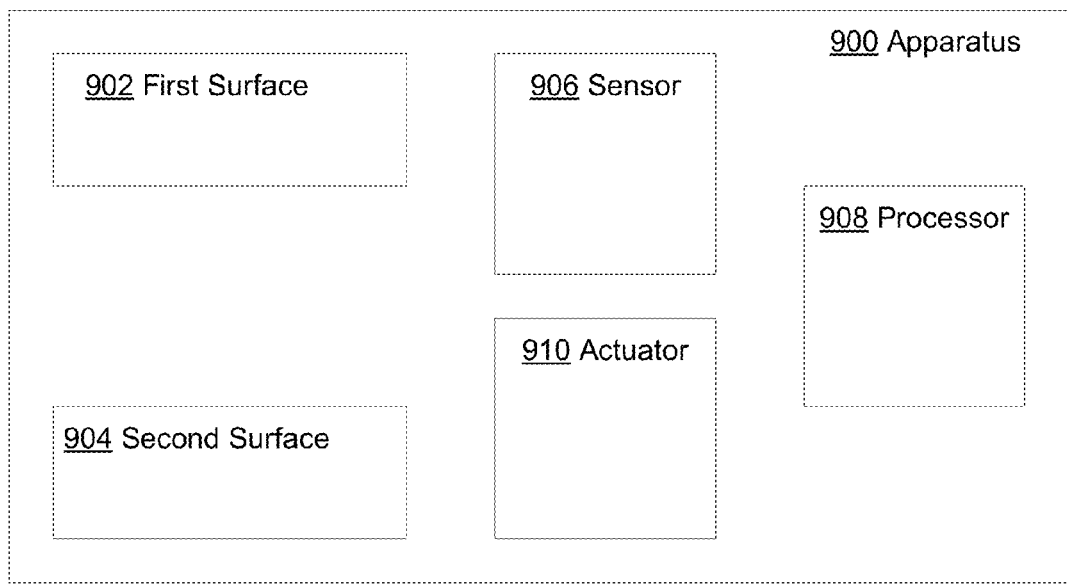
FIG. 9 is a block diagram of a system for sensing hand motion by measuring remote displacement according to one embodiment of the present invention.

FIG. 9 is a block diagram of a system for sensing hand motion by measuring remote displacement according to one embodiment of the present invention. According to the illustration in FIG. 9, the apparatus 900 comprises a first surface 902 and a second surface 904. Each of the surfaces 902, 904, is configured to engage a distal member of a surgical tool.

The apparatus 900 also comprises a sensor 906. The sensor 906 is configured to detect a relative movement of the first surface 902 and the second surface 904 about a pivot point. In one variation, the sensor comprises an optical sensor configured to measure the movement of the surfaces 902, 904. In other variations, sensor 906 may comprise an optical encoder, electrical encoder, magnetic encoder, or a hall effect sensor.

The sensor 906 is in communication with a processor 908. The processor 908 can be configured to receive a signal from the sensor. The processor 908 may be in communication with a medical simulator (not shown in FIG. 9).

The processor 908 is in communication with an actuator 910. The actuator can be configured to provide vibrotactile feedback to the apparatus 900. In one variation, the sensor detects a relative movement of the first surface 902 and the second surface 904, as a user operates a surgical tool engaged by the apparatus 900. The sensor 906 sends a signal based at least in part on the relative movement of the surfaces 902, 904 to the processor 908. The processor 908 subsequently sends an actuator signal to the actuator 910 based at least in part on the relative movement of the surfaces 902, 904. The actuator signal causes the actuator 910 to provide vibrotactile feedback to the apparatus 900, for example, by vibrating the surfaces 902, 904.

Figure 10:
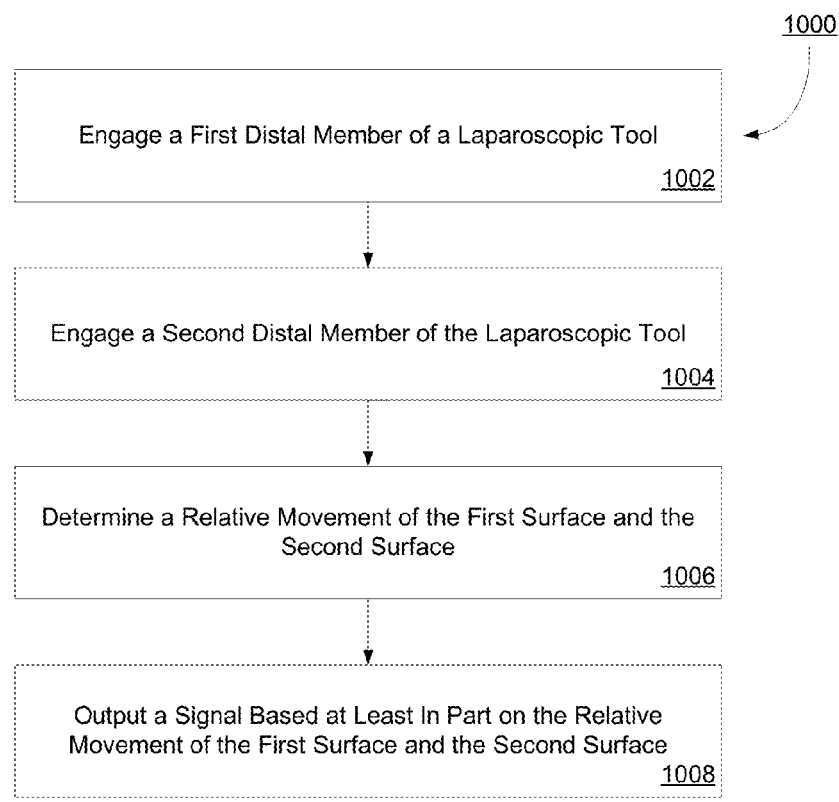
FIG. 10 is a flow diagram of a method for sensing hand motion by measuring remote displacement according to one embodiment of the present invention.

FIG. 10 is a flow diagram of a method for sensing hand motion by measuring remote displacement according to one embodiment of the present invention. In step 1002, the method comprises the step of engaging a first distal member of a laparoscopic tool at a first surface. In step 1004, the method comprises the step of engaging a second distal member of the laparoscopic tool at a second surface. The first surface and the second surface may be coupled at a pivot point.

Step 1006 comprises the step of determining a relative movement of the first surface and the second surface. A sensor, such as an optical sensor or a potentiometer, may determine the relative movement of the first surface and the second surface. Because the first distal member is engaged by the first surface 1002, and the second distal member is engaged by the second surface 1004, the relative movement of the first surface and the second surface may directly correspond to the relative movement of the first distal member and the second distal member.

Finally, step 1008 comprises the step of outputting a signal based at least in part on the relative movement of the first surface and the second surface. For example, a sensor 906 may output a signal to a processor 908.

Figure 11:
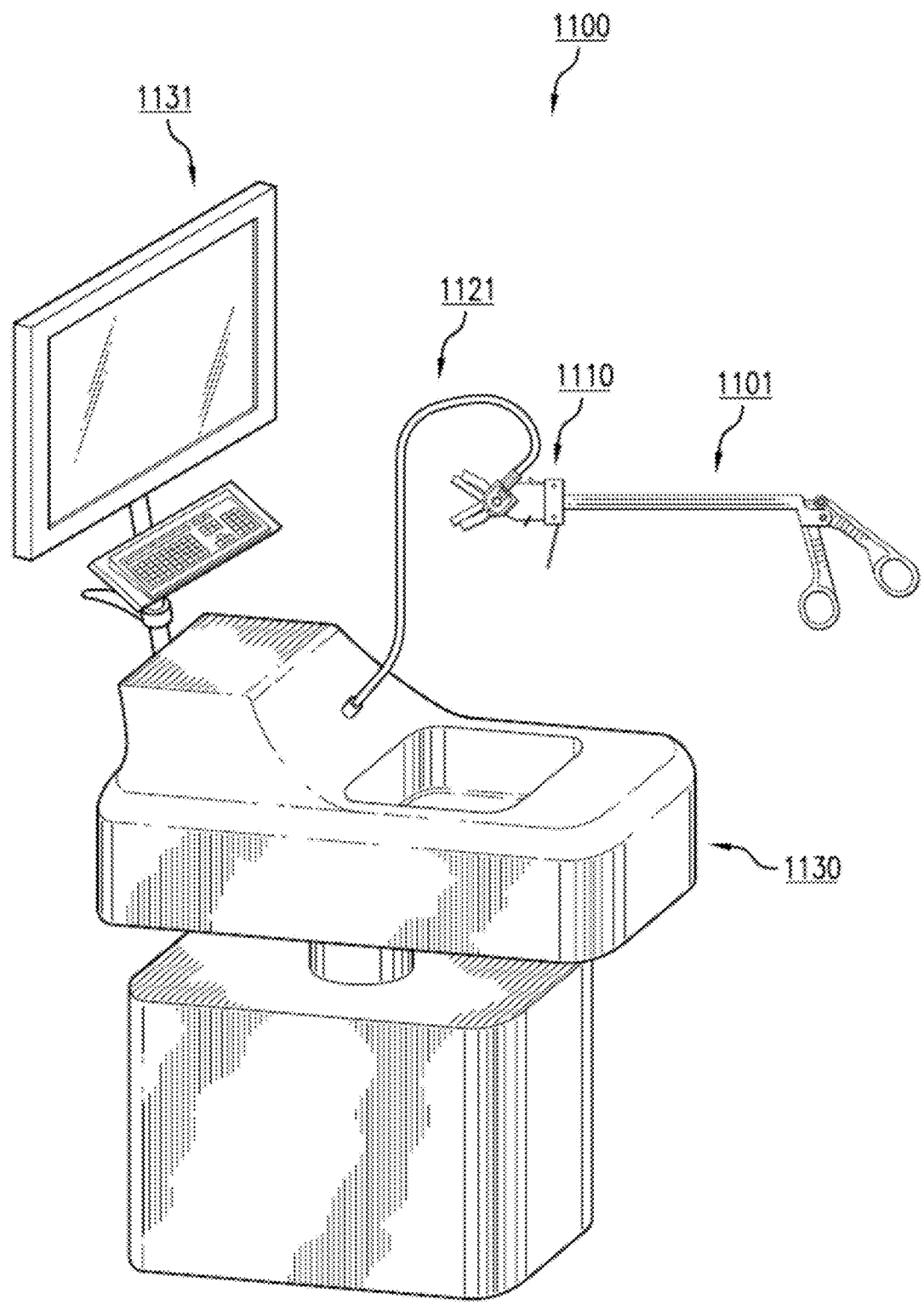
FIG. 11 is an illustration of a system for sensing hand motion by measuring remote displacement according to one embodiment of the present invention.

FIG. 11 is an illustration of a system for sensing hand motion by measuring remote displacement according to one embodiment of the present invention. The system 1100 in FIG. 11 comprises a surgical tool 1101, such as a laparoscopic tool. As shown in FIG. 11, the laparoscopic tool is engaged by an apparatus 1110 for sensing hand motion by measuring remote displacement.

The apparatus 1110 comprises a connecting mechanism 1121. As illustrated in FIG. 11, the connecting mechanism is a wire capable of transmitting signals to and from the apparatus 1110. For example, the apparatus 1110 may comprise a sensor (not shown in FIG. 11) configured to detect a relative movement of a first surface of the apparatus and a second surface of the apparatus engaging distal members of the laparoscopic tool 1101. The sensor may be configured to transmit signals via the connecting mechanism 1121 to a processor (not shown in FIG. 11). In another variation, the apparatus 1110 may comprise a wireless connecting mechanism.

As shown in FIG. 11, the apparatus 1110 is in communication with a medical simulator 1130. The medical simulator may comprise a processor (not shown in FIG. 11) and a display 1131. The display 1131 may be configured to show a simulation of a medical procedure, such as a laparoscopic surgery.

Embodiments of systems and methods for sensing hand motion by measuring remote displacement may provide various advantages over current medical simulators. In one embodiment, a system allows a medical simulator to track a user's manipulation of a surgical tool by measuring the displacement of the tool at the far end, or distal end, of the surgical tool. An apparatus may be attached to any real surgical tool. As one or both jaws, or distal members, of the surgical tool moves, each jaw independently pushes on a spring-loaded lever, or surface. A sensor can be configured to track the relative motion of each surface or lever moving in concert with the jaws.

Systems and methods for sensing hand motion by measuring remote displacement may be configured to operate with a variety of surgical tools with various operating parameters. For example, a system may be configured to accept a plurality of tools with different geometries, such as shaft diameters or distal member shapes or sizes. By measuring either symmetrical or asymmetrical movement of a surgical tool's distal members, and by being diameter-tolerant, the apparatus may be used with a wide variety of surgical tools.

In some embodiments, the sensation of using the surgical tool with the apparatus for sensing hand motion by measuring remote displacement is similar to or the same as using the surgical tool without the apparatus attached. For example, the apparatus may be lightweight, and cause little or no resistance on the jaws of the surgical tool. In some instances, the apparatus works passively, with little or no physical encumbrance to the surgical tool. The passive operation of the apparatus may be facilitated by spring-loaded members which engage each jaw of the surgical tool.

General

The foregoing description of the embodiments of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the invention.

That which is claimed:

1. An apparatus, comprising:
    a housing defining an interior cavity extending through an entire longitudinal length of the housing, the interior cavity configured to receive an elongated shaft of a laparoscopic tool;
        wherein the laparoscopic tool comprises:
            the elongated shaft, and
            a surgical tool positioned at a distal end of the elongated shaft, the surgical tool comprising a first distal member coupled to a second distal member at a first pivot point on the laparoscopic tool, wherein the first distal member comprises a first inner surface configured to contact a body part during a surgical procedure and a first outer surface opposite the first inner surface, and the second distal member comprises a second inner surface configured to contact the body part during the surgical procedure and a second outer surface opposite the second inner surface;
        the apparatus further comprising:
            a first pivotable member and a second pivotable member coupled to each other at a second pivot point, wherein the first pivotable member is configured to engage and move with the first outer surface of the first distal member of the laparoscopic tool, and the second pivotable member is configured to engage and move with the second outer surface of the second distal member of the laparoscopic tool;
            a first anchoring device coupled to the housing, the first anchoring device configured to secure the housing around the elongated shaft of the laparoscopic tool; and
            a sensor coupled to the first pivotable member and the second pivotable member, the sensor configured to detect a relative movement of the first pivotable member and the second pivotable member about the second pivot point and to generate a signal based at least in part on the relative movement.

2. The apparatus of claim 1, further comprising a processor in communication with the sensor and configured to receive the signal from the sensor.

3. The apparatus of claim 1, further comprising a flexure to apply a force about the second pivot point.

4. The apparatus of claim 1, further comprising a second anchoring device coupled to the housing, the second anchoring device configured to secure the housing around the elongated shaft.

5. The apparatus of claim 4, wherein the first anchoring device is configured to secure the housing to the elongated shaft of the laparoscopic tool by applying pressure to the elongated shaft in response to a spring force applied by a spring coupled to the housing and the first anchoring device, and wherein the second anchoring device is configured to secure the housing to the elongated shaft by applying pressure to the elongated shaft in response to a different spring force applied by a different spring coupled to the housing and the second anchoring device.

6. The apparatus of claim 5, wherein the first anchoring device and the second anchoring device are configured to accept a plurality of surgical tools, each of the plurality of surgical tools having a different diameter.

7. The apparatus of claim 5, wherein a first position of the first anchoring device is adjustable independent of the second anchoring device, and a second position of the second anchoring device is adjustable independent of the first anchoring device.

8. The apparatus of claim 1, further comprising an actuator positioned on the apparatus and configured for providing vibrotactile feedback in response to an actuator signal.

9. The apparatus of claim 1, wherein the first distal member and the second distal member are configured to move symmetrically.

10. The apparatus of claim 1, wherein the first distal member and the second distal member are configured to move asymmetrically.

11. The apparatus of claim 1, wherein the sensor comprises a potentiometer, an optical encoder, electrical encoder, magnetic encoder, or a hall effect sensor.

12. The apparatus of claim 1, wherein the sensor is in communication with a medical simulation device.

13. The apparatus of claim 1, wherein the apparatus comprises a lightweight plastic or resin material.

14. The apparatus of claim 1, wherein the first pivotable member is configured to engage the first distal member of the laparoscopic tool by sliding over the first outer surface of the first distal member of the laparoscopic tool.

15. The apparatus of claim 1, wherein the first pivotable member comprises an open loop configured to slideably engage the first distal member of the laparoscopic tool such that the first distal member enters one side of the open loop and protrudes out another side of the open loop.

16. The apparatus of claim 1, wherein:
    the first pivotable member is configured to contact the first outer surface of the first distal member of the laparoscopic tool;
    the second pivotable member is configured to contact the second outer surface of the second distal member of the laparoscopic tool; and
    the first inner surface and the second inner surface are configured to grasp the body part during the surgical procedure.

17. A method, comprising:
    positioning at least a portion of an elongated shaft of a laparoscopic tool throughout an interior cavity traversing an entire longitudinal length of a housing of an apparatus;
        wherein the laparoscopic tool comprises:
            the elongated shaft, and
            a surgical tool positioned at a distal end of the elongated shaft, the surgical tool comprising a first distal member coupled to a second distal member at a first pivot point on the laparoscopic tool, wherein the first distal member comprises a first inner surface configured to contact a body part during a surgical procedure and a first outer surface opposite the first inner surface, and the second distal member comprises a second inner surface configured to contact the body part during the surgical procedure and a second outer surface opposite the second inner surface;
    engaging the first outer surface of the first distal member of the laparoscopic tool with a first pivotable member of the apparatus such that the first distal member and the first pivotable member move in unison;
    engaging the second outer surface of the second distal member of the laparoscopic tool with a second pivotable member of the apparatus such that the second distal member and the second pivotable member move in unison, wherein the first pivotable member is coupled to the second pivotable member at a second pivot point on the apparatus;

securing, by an anchoring device coupled to the housing, the housing around the elongated shaft of the laparoscopic tool such that the elongated shaft extends through the entire longitudinal length of the housing;

determining, by a sensor coupled to the first and the second pivotable members, a relative movement of the first pivotable member and the second pivotable member; and outputting, by the sensor, a signal based at least in part on the relative movement of the first pivotable member and the second pivotable member.

18. The method of claim 17, further comprising:
providing haptic feedback to the laparoscopic tool based at least in part on the signal.

19. An apparatus configured to detect the relative motion of a laparoscopic tool, the laparoscopic tool comprising:
an elongated shaft, and
a surgical tool positioned at a distal end of the elongated shaft, the surgical tool comprising a first distal member coupled to a second distal member at a first pivot point on the laparoscopic tool, wherein the first distal member comprises a first inner surface configured to contact a body part during a surgical procedure and a first outer surface opposite the first inner surface, and the second distal member comprises a second inner surface configured to contact the body part during the surgical procedure and a second outer surface opposite the second inner surface;
wherein the apparatus comprises:
a housing defining an interior cavity disposed through an entire longitudinal length of the housing, the interior cavity configured to receive the elongated shaft of the laparoscopic tool;
a first pivotable member and a second pivotable member coupled to each other at a second pivot point on the housing, wherein the first pivotable member is configured to engage and move with the first outer surface of the first distal member of the laparoscopic tool, and the second pivotable member is configured to engage and move with the second outer surface of the second distal member of the laparoscopic tool;
an anchoring device coupled to the housing, the anchoring device configured to secure the apparatus around the elongated shaft of the laparoscopic tool;
a sensor coupled to the first pivotable member and the second pivotable member and in communication with a laparoscopic simulator device, the sensor configured to measure a relative movement of the first pivotable member and the second pivotable member and transmit a movement signal based at least in part on the relative movement to the laparoscopic simulator device;
an actuator positioned on the apparatus and configured to output vibrotactile feedback; and
a processor positioned on the apparatus and in communication with the sensor and the actuator, the processor configured to receive the movement signal from the sensor and transmit an actuator signal to the actuator based at least in part on the movement signal, the actuator signal configured to cause the actuator to output the vibrotactile feedback.

20. A system, comprising:
a laparoscopic surgical tool comprising:
an elongated shaft; and
a surgical tool positioned at a distal end of the elongated shaft, the surgical tool comprising a first distal member coupled to a second distal member at a first pivot point on the laparoscopic tool, wherein the first distal member comprises a first inner surface configured to contact a body part during a surgical procedure and a first outer surface opposite the first inner surface, and the second distal member comprises a second inner surface configured to contact the body part during the surgical procedure and a second outer surface opposite the second inner surface; and
an apparatus comprising:
a housing defining an interior cavity disposed through an entire longitudinal length of the housing, wherein the elongated shaft of the laparoscopic tool is positioned through the entire longitudinal length of the housing;
a first pivotable member and a second pivotable member coupled to each other at a second pivot point on the housing, wherein the first pivotable member is configured to engage and move with the first outer surface of the first distal member of the laparoscopic tool, and the second pivotable member is configured to engage and move with the second outer surface of the second distal member of the laparoscopic;
an anchoring device coupled to the housing, the anchoring device configured to secure the apparatus around the elongated shaft of the laparoscopic surgical tool; and
a sensor coupled to the first pivotable member and the second pivotable member, the sensor configured to detect a relative movement of the first pivotable member and the second pivotable member about the second pivot point and to generate a sensor signal based at least in part on the relative movement.

21. The system of claim 20, wherein the laparoscopic surgical tool is configured to be hand-held.

* * * * *